United States Patent [19]

Jancis et al.

[11] Patent Number: 4,664,845

[45] Date of Patent: May 12, 1987

[54] PHENYLENEDIAMINE SOLUBILIZER FOR DINITROPHENOL IN AROMATIC SOLVENT

[75] Inventors: Elmar H. Jancis, Naugatuck; Paul E. Stott, Sandy Hook, both of Conn.

[73] Assignee: Uniroyal Chemical Company, Inc., Middlebury, Conn.

[21] Appl. No.: 817,324

[22] Filed: Jan. 19, 1986

[51] Int. Cl.$^4$ .............................................. C09K 15/24
[52] U.S. Cl. .................................. 252/401; 252/403; 564/307; 568/711; 203/9
[58] Field of Search .................... 564/307; 568/711; 252/401, 403, 364, 577; 203/9

[56] References Cited

U.S. PATENT DOCUMENTS

| | | | |
|---|---|---|---|
| 2,526,567 | 10/1950 | Drake et al. | 570/104 |
| 2,943,075 | 6/1960 | Schweitzer, Jr. | 568/711 X |
| 3,366,702 | 1/1968 | Moriarty | 203/9 X |
| 3,420,778 | 1/1969 | Heidt | 252/577 X |
| 3,770,694 | 11/1973 | Berg et al. | 252/401 X |
| 4,051,067 | 9/1977 | Wilder | 252/401 |
| 4,105,506 | 8/1978 | Watson | 203/9 |
| 4,132,603 | 1/1979 | Watson | 203/9 |
| 4,272,344 | 6/1981 | Watson | 203/9 X |
| 4,376,221 | 3/1983 | Jackisch | 252/401 X |
| 4,457,806 | 7/1984 | Grivas et al. | 203/9 |
| 4,466,905 | 8/1984 | Butler et al. | 252/403 |
| 4,468,343 | 8/1984 | Butler et al. | 252/403 |
| 4,568,711 | 2/1986 | Kay et al. | 252/401 X |

*Primary Examiner*—John F. Terapane
*Assistant Examiner*—Matthew A. Thexton
*Attorney, Agent, or Firm*—William E. Dickheiser

[57] ABSTRACT

Compositions, comprised of a dinitrophenol in an aromatic hydrocarbon solvent, which compositions further comprise a sufficient amount of a phenylenediamine such that a greater amount of dinitrophenol is in solution than would be present in solution if such phenylenediamine were not present, exhibit unexpectedly desirable low temperature stability, and may be diluted with additional solvent to be employed as polymerization inhibitors for vinyl aromatic compounds.

17 Claims, No Drawings

PHENYLENEDIAMINE SOLUBILIZER FOR DINITROPHENOL IN AROMATIC SOLVENT

FIELD OF THE INVENTION

This invention relates to a liquid composition comprised of a dinitrophenol in an aromatic hydrocarbon solvent, which composition further comprises a sufficient amount of a phenylenediamine such that a greater amount of such dinitrophenol is in solution than would be present in solution if such phenylenediamine were not present. This composition, which exhibits unexpectedly desirable low temperature stability, may be diluted with additional solvent to be employed as a polymerization inhibitor for vinyl aromatic compounds.

BACKGROUND OF THE INVENTION

Commercial processes for the manufacture of vinyl aromatic compounds such as monomeric styrene, divinyl benzene and lower alkylated styrenes (such as alphamethylstyrene and vinyltoluene) typically produce products contaminated with various impurities, such as benzene, toluene and the like. These impurities must be removed in order for the monomer product to be suitable for most applications. Such purification of vinyl aromatic compounds is generally accomplished by distillation.

However, it is well known that vinyl aromatic compounds polymerize readily and that the rate of polymerization increases rapidly as the temperature increases. In order to prevent polymerization of the vinyl aromatic monomer under distillation conditions various polymerization inhibitors have been employed.

In general, the compounds which are commercially employed as such polymerization inhibitors are of the dinitrophenolic class. Thus, for example, Drake et al, in U.S. Pat. No. 2,526,567, show the stabilization of nuclear chlorostyrenes employing 2,6-dinitrophenols. Similarly, U.S. Pat. No. 4,105,506, to Watson, discloses the use of 2,6-dinitro-p-cresol as a polymerization inhibitor for vinyl aromatic compounds.

More recently, it has been disclosed by Butler et al, in U.S. Pat. No. 4,466,905, that, in the presence of oxygen, the presence of phenylenediamines in the distillation column with 2,6-dinitro-p-cresol will further reduce the amount of polmyerization which occurs.

While dinitrophenols are effective polymerization inhibitors, there are several disadvantages associated with their use. For example, dinitrophenols are solids that, if subjected to temperatures above their melting points, are unstable and may explode (see U.S. Pat. No. 4,457,806). Thus the bulk shipment and storage of these materials as solids is precluded.

Accordingly, it is necessary to ship and store these inhibitors as a solution, preferably in a solvent compatible with vinyl aromatic monomer processing, typically a low boiling hydrocarbon solvent. Unfortunately, most dinitrophenols have low solubilities in such preferred solvents in the range of temperatures to which they are likely to be exposed during shipment and storage. For example, the solubility of 2,6-dinitro-para-cresol is about 20 percent by weight in ethylbenzene at 18° C. This figure decreases rapidly as temperatures drop, with such compound being 15% soluble at −2° C., 10% at −14° C. and only 4.2% soluble at −25° C. Once precipitated from solution, these dinitrophenol compounds do not readily return to solution, even when the temperature is returned to more normal storage temperature (e.g. of about 18° C.).

Moreover, dinitrophenols are highly toxic, having an $LD_{50}$(rat) of less than 30 mg/Kg (Sax, Hazardous Properties of Industrial Chemicals).

The high toxicity and low solubility of such dinitrophenolic inhibitors coupled with the flammability of the solvents employed render the shipment and storage of solutions of dinitrophenolic inhibitors in their preferred solvents expensive and somewhat hazardous. Further, if the inhibitor precipitates from solution due to low temperatures during shipment or storage, the actual concentration may fall far below the stated concentration. If such inhibitor solution gets changed to a vinyl aromatic distillation column on the basis of its stated concentration, the low level of inhibitor actually reaching the distillation column can result in catastrophic failure of the distillation column due to explosive polymerization of the vinyl aromatic monomer.

It would, therefore, be desirable to possess a concentrated solution of dinitrophenol which thus could be more safely and economically shipped. Moreover, it would be desirable to possess a concentrated solution of dinitrophenol which would exhibit desirable low temperature stability.

Accordingly, it is an object of this invention to a provide concentrated solution of dinitrophenol, which concentrated solution possesses a lower flash point than conventional nonconcentrated solutions, and which may therefore be transported more safely.

It is another object of this invention to provide a concentrated solution of dinitrophenol which will require less volume of solvent per given amount of dinitrophenol and which may therefore be more economically shipped.

It is a further object of this invention to provide a dinitrophenol solution which exhibits desirable low temperature stability.

The foregoing and additional objects will become more fully apparent from the following description and accompanying Examples.

DESCRIPTION OF THE INVENTION

In one aspect, this invention is directed to a liquid composition comprising a dinitrophenol of the formula:

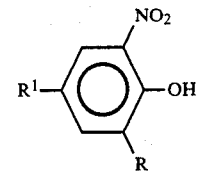

wherein one of R and $R^1$ is nitro and the other is selected from the group consisting of hydrogen, chlorine and $C_1$-$C_8$ alkyl;
dissolved in an aromatic hydrocarbon solvent, said liquid composition futher comprising a sufficient amount of a phenylenediamine of the formula:

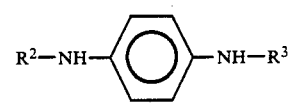

wherein R² and R³ are each independently selected from the group consisting of hydrogen, C₁–C₁₂ alkyl, phenyl, and phenyl substituted with C₁–C₈ alkyl, such that the amount of dinitrophenol which is dissolved in said solvent is greater than the amount of dinitrophenol which could be dissolved in said solvent if such phenylenediamine were not present.

In another aspect, this invention relates to a low temperature-stable liquid composition comprising:

(A) a dinitrophenol of the formula:

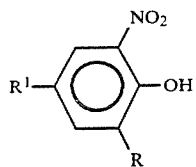

wherein one of R and R¹ is nitro and the other is selected from the group consisting of hydrogen, chlorine and C₁–C₈ alkyl:

(B) a phenylenediamine of the formula:

wherein R² and R³ are each independently selected from the group consisting of hydrogen, C₁–C₁₂ alkyl, phenyl, and phenyl substituted with C₁–C₈ alkyl; and (C) an aromatic hydrocarbon solvent:
wherein the weight ratio of component A to component B is between about 1:9 and about 9:1; and
wherein the weight ratio of Component A plus Component B to Component C is at least about 1:10.

The compositions of this invention are comprised of three components—i.e., a dinitrophenol, a phenylenediamine and an aromatic hydrocarbon solvent.

The dinitrophenols which may be employed are compounds having the structure:

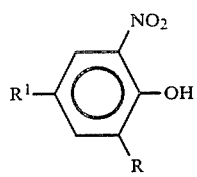

wherein one of R and R¹ is nitro and the other is selected from the group consisting of hydrogen and C₁–C₈ straight chain or branched alkyl. Preferred dinitrophenols include 2,6-dinitro-p-cresol, 4,6-dinitro-o-cresol, 2,6-dinitro-p-isopropylphenol, 4,6-dinitro-o-isopropylphenol, and 4,6-dinitro-o-sec-butylphenol.

The phenylenediamine compounds which may be employed are of the formula:

wherein R² and R³ are each independently selected from the group consisting of hydrogen, C₁–C₁₂ straight chain or branched alkyl, phenyl, and phenyl substituted with C₁–C₈ alkyl. In general, preferred phenylene diamines are compounds having the above structure wherein R² is phenyl and R³ is C₃–C₈ alkyl. Illustrative preferred phenylene diamines which may be employed include N-phenyl-N'-isopropyl-p-phenylenediamine, N-phenyl-N'-(1,3-dimethylbutyl)-p-phenylenediamine, N-phenyl-N'-(1,3-dimethylpentyl)-p-phenylenediamine, N,N'-diisopropyl-p-phenylenediamine, N,N'-di-sec-butyl-p-phenylenediamine. and N,N'-bis(1,4-dimethylpentyl)-p-phenylenediamine.

The aromatic hydrocarbon solvent which can be employed may be any liquid aromatic hydrocarbon in which the dinitrophenol and phenylenediamine components are soluble. Illustrative of such solvents are benzene, toluene, xylene, ethylbenzene, styrene, vinyltoluene, divinylbenzene, alpha-methylstyrene and other alkylated styrenes or alkyl-benzenes, all of which materials are commercially available.

While the most preferred solvent will vary with the particular application in which the stabilizer composition of this invention is to be employed, typically the vinyl aromatic to be stabilized and its hydrogenated precursor are the preferred solvents. Thus, for the stabilization of styrene, ethylbenzene and styrene itself are the preferred solvents. Similarly for the stabilization of alpha-methylstyrene, isopropylbenzene and alpha-methylstyrene are the preferred solvents.

The phenylenediamine is present in an amount such that the amount of dinitrophenol which is dissolved in said solvent is greater than the amount of dinitrophenol which could be dissolved in said solvent if such phenylenediamine were not present. Accordingly, the amount of dinitrophenol which is actually present in the composition of this invention is greater than the amount which could be dissolved in the aromatic solvent selected at a given temperature if the phenylenediamine were not present.

Typically, the weight ratio of dinitrophenol plus phenylenediamine to aromatic hydrocarbon solvent is at least about 1:10. Preferably such ratio is between about 1:4 and about 2:1, although, as will be recognized by one skilled in the art, the preferred ratio will be dependent upon the particular components selected as well as upon the temperatures and pressures to which the composition ratios of dinitrophenol to phenylenediamine will generally range between about 9:1 and about 1:9, and will preferably range between about 3:2 and about 2:3.

The compositions of this invention may be prepared by adding the desired amounts of dinitrophenol and phenylenediamine, in any order, to a measured amount of solvent. Preferably, such addition takes place under agitation.

Moreover, the compositions of this invention exhibit desirable low temperature stability, with frequently at least about 75 percent or more of the total amount of dinitrophenol plus phenylenediamine which are soluble in a given solvent at 18° C. being retained in solution in the same solvent at −25° C.

The compositions of this invention may be employed as polymerization inhibitors by diluting them with additional amounts of solvent so that a concentration of no greater than about 5 weight percent is present, such dilute concentrations being readily fed into the vinyl aromatic reactor distillation column.

EXAMPLES

The following Examples are intended to further illustrate the present invention and are not intended to limit the scope of the invention in any manner whatsoever.

EXAMPLE 1

The solubilities of 4,6-dinitro-ortho-cresol (DNOC), 2,6-dinitro-para-cresol (DNPC), N-isopropyl-N'-phenyl-p-phenylenediamine (Naugard I-4, a trademark of Uniroyal Chemical Company, Inc., hereinafter "I-4"), and blends of DNOC or DNCP with I-4 in ethylbenzene were determined for a wide range of temperatures by making suspensions of the pure products, filtering off the undissolved substrate and calculating the solubility by weight difference. The results of such testing are listed in Table I below:

TABLE I

| | Percent Solubility in Ethylbenzene | | | |
|---|---|---|---|---|
| Solute | 18° C. | −2° C. | −14° C. | −25° C. |
| DNOC | 19 | 12 | 10 | 4.5 |
| DNPC | 20 | 15 | 10 | 4.2 |
| I-4 | 27 | 16 | 12.5 | 8.2 |
| DNOC/I-4 1/1 by weight | 67+ | 66 | 56 | 53 |
| DNPC/I-4 1/1 by weight | 67+ | 66 | 63 | 58 |

EXAMPLE 2

Following the procedure described in Example 1, the solubilities of DNOC, DNPC, I-4 and blends of DNOC or DNPC with I-4 in styrene were determined. The results of such testing are summarized in Table II below.

TABLE II

| | Percent Solubility in Styrene | | | |
|---|---|---|---|---|
| Solute | 18° C. | −2° C. | −14° C. | −25° C. |
| DNOC | 25 | 25 | 13 | 6.1 |
| DNPC | 25 | 25 | 25 | 18 |
| I-4 | 30 | 24 | 19 | 14.5 |
| DNOC/I-4 1/1 by weight | 67+ | 67+ | 67+ | 67+ |
| DNPC/I-4 1/1 by weight | 67+ | 67+ | 67+ | 67+ |

The above data in Tables I and II indicate that the presence of the phenylenediamine (I-4) allows increased amounts of dinitrophenol to be dissolved into the aromatic hydrocarbon solvent.

Thus, for example, at −25° C. a 1:1 mixture of DNPC and I-4 is 58% soluble in ethylbenzene, whereas individually, the solubilities of these compounds in such solvent at such temperature are only 4.2% and 8.2% respectively. Thus the mixture is almost 4 times more soluble than the additive amount, with almost 8 times more DNPC in solution.

Moreover, the above data also indicate the low temperature stability of the compositions of this invention. Thus, a 1:1 solution of DNPC and I-4 in ethylbenzene retains about 87% of its solubility at −25° C. relative to its solubility at 18° C. In contrast solutions of DNPC and I-4 alone retain only about 21% and about 30% of their solubilities over the same temperature range.

What is claimed is:

1. A liquid composition comprising a dinitrophenol of the formula:

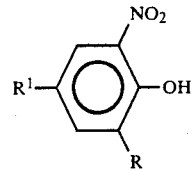

wherein one of R and $R^1$ is nitro and the other is selected from the group consisting of hydrogen, chlorine and $C_1$–$C_8$ alkyl;
dissolved in an aromatic hydrocarbon solvent, said liquid composition futher comprising a sufficient amount of a phenylenediamine of the formula:

wherein $R^2$ and $R^3$ are each independently selected from the group consisting of hydrogen, $C_1$–$C_{12}$ alkyl, phenyl, and phenyl substituted with $C_1$–$C_8$ alkyl;
such that the amount of dinitrophenol which is dissolved in said solvent is greater than the amount of dinitrophenol which could be dissolved in said solvent if such phenylenediamine were not present.

2. The composition of claim 1 wherein said dinitrophenol is selected from the group consisting of 2,6-dinitro-p-cresol, 4,6-dinitro-o-cresol, 2,6-dinitro-p-isopropylphenol, 4,6-dinitro-o-isopropylphenol, and 4,6-dinitro-o-sec-butylphenol.

3. The composition of claim 1 wherein said phenylenediamine is selected from the group consisting of N-phenyl-N'-isopropyl-p-phenylenediamine, N-phenyl-N'-(1,3-dimethylbutyl)-p-phenylenediamine, N-phenyl-N'-(1,3-dimethylpentyl)-p-phenylenediamine, N,N'-diisopropyl-p-phenylenediamine, N,N'-di-sec-butyl-p-phenylenediamine and N,N'-bis(1,4-dimethylpentyl)-p-phenylenediamine.

4. The composition of claim 1 wherein said aromatic hydrocarbon solvent is selected from the group consisting of benzene, toluene, xylene, ethylbenzene, styrene, vinyltoluene, divinylbenzene and alphamethylstyrene.

5. The composition of claim 4 wherein said aromatic hydrocarbon is selected from the group consisting of styrene and ethylbenzene.

6. The composition of claim 1 the weight ratio of dinitrophenol plus phenylenediamine to aromatic hydrocarbon solvent is between about 1:4 and about 2:1.

7. The composition of claim 1 wherein the weight ratio of dinitrophenol to phenylenediamine is between about 2:3 and 3:2.

8. A low temperature-stable liquid composition comprising:
(A) a dinitrophenol of the formula:

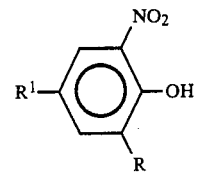

wherein one of R and R[1] is nitro and the other is selected from the group consisting of hydrogen, chlorine and $C_1$–$C_8$ alkyl:

(B) a phenylenediamine of the formula:

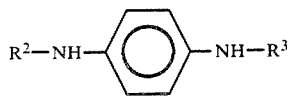

wherein $R^2$ and $R^3$ are each independently selected from the group consisting of hydrogen, $C_1$–$C_{12}$ alkyl, phenyl, and phenyl substituted with $C_1$–$C_8$ alkyl; and (C) an aromatic hydrocarbon solvent;

wherein the weight ratio of component A to component B is between about 1:9 and about 9:1; and wherein the weight ratio of Component A plus Component B to Component C is at least about 1:10.

9. The composition of claim 8 wherein said dinitrophenol is selected from the group consisting of 2,6-dinitro-p-cresol, 4,6-dinitro-o-cresol, 2,6-dinitro-p-isopropylphenol, 4,6-dinitro-o-isopropylphenol, and 4,6-dinitro-o-sec-butylphenol.

10. The composition of claim 8 wherein said phenylenediamine is selected from the group consisting of N-phenyl-N'-isopropyl-p-phenylenediamine, N-phenyl-N'-(1,3-dimethylbutyl)-p-phenylenediamine, N-phenyl-N'-(1,3-dimethylpentyl)-p-phenylenediamine, N,N'-diisopropyl-p-phenylenediamine, N,N'-di-sec-butyl-p-phenylenediamine and N,N'-bis(1,4-dimethylpentyl)-p-phenylenediamine.

11. The composition of claim 8 wherein said aromatic hydrocarbon solvent is selected from the group consisting of benzene, toluene, xylene, ethylbenzene, styrene, vinyltoluene, divinylbenzene and alphamethylstyrene. methylstyrene.

12. The composition of claim 8 wherein said aromatic hydrocarbon is selected from the group consisting of styrene and ethylbenzene.

13. The composition of claim 8 the weight ratio of dinitrophenol plus phenylenediamine to aromatic hydrocarbon solvent is between about 1:4 and about 2:1.

14. The composition of claim 8 wherein the weight ratio of dinitrophenol to phenylenediamine is between about 2:3 and 3:2.

15. The composition of claim 8 wherein said dinitrophenol is selected from the group consisting of 2,6-dinitro-p-cresol, 4,6-dinitro-o-cresol, 2,6-dinitro-p-isopropylphenol, 4,6-dinitro-o-isopropylphenol, and 4,6-dinitro-o-sec-butylphenol;

wherein said phenylenediamine is selected from the group consisting of N-phenyl-N'-isopropyl-p-phenylenediamine, N-phenyl-N'-(1,3-dimethylbutyl)-p-phenylenediamine, N-phenyl-N'-(1,3-dimethylpentyl)-p-phenylenediamine, N,N'-diisopropyl-p-phenylenediamine, N,N'-di-sec-butylphenylenediamine and N,N'-bis(1,4-dimethylpentyl)-p-phenylenediamine; and wherein said aromatic hydrocarbon solvent is selected from the group consisting of benzene, toluene, xylene, ethylbenzene, styrene, vinyltoluene, divinylbenzene and alpha-methylstyrene.

16. The composition of claim 15 the weight ratio of dinitrophenol plus phenylenediamine to aromatic hydrocarbon solvent is between about 1:4 and about 2:1.

17. The composition of claim 15 wherein the weight ratio of dinitrophenol to phenylenediamine is between about 2:3 and 3:2.

* * * * *

UNITED STATES PATENT AND TRADEMARK OFFICE
CERTIFICATE OF CORRECTION

PATENT NO. : 4,664,845

DATED : May 12, 1987

INVENTOR(S) : Elmar H. Jancis et al

It is certified that error appears in the above-identified patent and that said Letters Patent is hereby corrected as shown below:

On the Title page, item [22], the filing date should read "January 9, 1986".

Signed and Sealed this

Eighth Day of June, 1993

Attest:

MICHAEL K. KIRK

*Attesting Officer*   *Acting Commissioner of Patents and Trademarks*